United States Patent [19]
Van Belle et al.

[11] Patent Number: 5,840,896
[45] Date of Patent: Nov. 24, 1998

[54] METHOD OF PREVENTING OR LIMITING REPERFUSION DAMAGE

[75] Inventors: Herman Van Belle; Willy Joannes Carolus Van Laerhoven, both of Beerse, Belgium

[73] Assignee: Janssen Pharmaceutica, N.V., Beerse, Belgium

[21] Appl. No.: 424,687

[22] Filed: Apr. 18, 1995

Related U.S. Application Data

[60] Division of Ser. No. 730,836, filed as PCT/EP90/01985, Nov. 19, 1990, abandoned, which is a continuation-in-part of Ser. No. 440,142, Nov. 22, 1989, abandoned.

[51] Int. Cl.$^6$ .................................................. C07D 241/04
[52] U.S. Cl. ........................ 544/390; 544/396; 544/397; 544/400
[58] Field of Search ............................................... 544/390

[56] References Cited

U.S. PATENT DOCUMENTS

| | | | |
|---|---|---|---|
| 4,766,125 | 8/1988 | Van Daele | 514/255 |
| 4,880,808 | 11/1989 | Van Daele et al. | 514/255 |
| 4,968,684 | 11/1990 | Van Daele et al. | 514/255 |
| 5,026,853 | 6/1991 | Van Daele et al. | 544/390 |

FOREIGN PATENT DOCUMENTS 0 285 219  10/1988  European Pat. Off. .

OTHER PUBLICATIONS

Van Belle et al., CA 111, No. 167017h (1989).
Flameng et al., CA 102, No. 214829 (1985).
Xhonneux et al., CA 105, No. 202980 (1986).
Wood et al., CA 103, No. 189487 (1985).
Liu et al., CA 105, No. 108208 (1986).
Van Belle et al., J. Mol. Cell Cardiol. 21 (Supp. 2) 1989, Abstract 424.
Wainwright et al., Br. J. Pharmacol., 99, Proc. Suppl. 1990 (Abstract).
Ijzerman et al., *European Journal of Pharmacology* — Molecular Pharmacology Section, 172 (1989) 273–281.
Van Belle et al, *J. Cell. Cardiol.* 21, pp. 797–805 (1989).
*Stereochemistry of Carbon Compounds* by Ernest L. Eliel, pp. 68–74 (1962).

*Primary Examiner*—Emily Bernhardt
*Attorney, Agent, or Firm*—Ellen Ciambrone Coletti

[57] ABSTRACT

There is disclosed a process for preparing (l)-(−)-2-aminocarbonyl-N-(4-amino-2,6-dichlorophenyl)-4-[5,5-bis(4-fluorophenyl)pentyl]-1-piperazineacetamide which comprises the steps of (a) cyclizing (−)-(S,S)-N$^1$,N$^2$-bis(1-phenylethyl)-1,2-ethanediamine with 2,3-dibromopropanamide in a reaction-inert solvent in the presence of a base, thus yielding an intermediate; (b) resolving the intermediate of into two stereoisomers and recovering thereby [1(S),2A,4(S)]-1,4-bis(1-phenylethyl)-2-piperazinecarboxamide; (c) hydrogenolyzing [1(S),2A,4(S)]- 1,4-bis(1-phenylethyl)-2-piperazinecarboxamide under a hydrogen atmosphere in an alkanol in the presence of a hydrogenation catalyst to produce (+) -2-piperazinecarboxamide; (d) reductively N-alkylating (+)-2-piperazinecarboxamide with 5,5-bis(4-fluorophenyl)pentaldehyde under a hydrogen atmosphere in an alkanol in the presence of a hydrogenation catalyst to produce a compound of the formula:

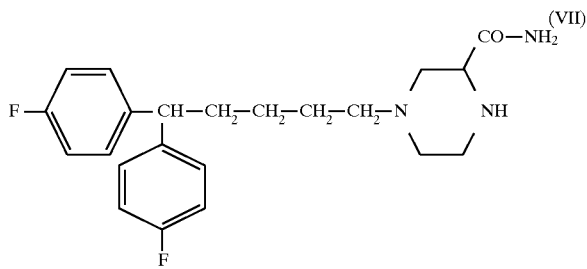

(VII)

(e) N-alkylating the compound of Formula (VII) with an alkylating reagent of the formula:

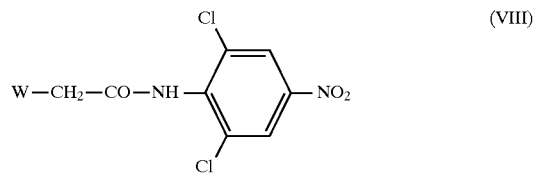

(VIII)

wherein W represents a reactive leaving group, in a reaction-inert solvent in the presence of a base to form the nitro analog of the desired compound; and (f) reducing the nitro compound in the presence of a reducing agent in a reaction-inert solvent.

11 Claims, No Drawings

METHOD OF PREVENTING OR LIMITING REPERFUSION DAMAGE

CROSS-REFERENCE TO RELATED APPLICATIONS

This application is a divisional of application Ser. No. 07/730,836, filed on Jul. 12, 1991 now abandoned, which was based upon PCT application Serial No. PCT/EP 90/01985, filed Nov. 19, 1990, which claims priority as a continuation-in-part from U.S. application Ser. No. 07/440, 142, filed on Nov. 22, 1989 now abandoned.

A recurring problem during reperfusion, i.e. the restoration of blood flow through tissue or organs previously deprived of blood supply, (e.g. after thrombolysis, in hearts after open heart surgery or in hearts for transplantation) is the further degeneration of this tissue or organ by leukocytes and their cytotoxic products.

The present invention provides a novel method of preventing or limiting reperfusion damage by application of particular N-aryl-piperazinealkanamide derivatives and also a novel method for preserving hearts for transplantation significantly longer.

Some compounds which can be used in the present invention are known from U.S. Pat. No. 4,766,125 as agents useful for protecting the heart from myocardial injury caused by ischaemia, anoxia or hypoxia.

Some compounds are also described in U.S. Pat. No. 4,880,808 as useful therapeutical agents which improve sleep and counteract sleep disorders.

The present invention is concerned with a method of preventing and/or limiting reperfusion damage upon reperfusion of an organ or muscular tissue wherein blood perfusion is diminished or absent, which method comprises administering to said organ or muscular tissue an effective reperfusion damage preventing and/or limiting amount of a compound having the formula $$L-N\underset{\underset{}{\diagdown}}{\diagup}\overset{R^1}{\diagdown}N-CH_2-\overset{O}{\overset{\|}{C}}-\overset{}{\underset{H}{N}}-Ar, \quad (I)$$

a stereochemically isomeric form thereof or a pharmaceutically acceptable acid addition salt form thereof, wherein L is a radical of formula $$-CH_2-CH_2-CH_2-CH_2-\underset{\underset{Ar^2}{|}}{CH}-Ar^1, \quad (a)$$

$$-CH_2-CH_2-CH_2-CH=\underset{\underset{Ar^2}{|}}{C}-Ar^1, \quad (b)$$

$$-CH_2-CH_2-CH_2-O-\underset{\underset{Ar^2}{|}}{CH}-Ar^1, \quad (c)$$

$$-CH_2-CH_2-CH_2-CH_2-\underset{\underset{CO-Ar^2}{|}}{N}-Ar^1, \quad (d)$$

$$-CH_2-CH_2-CH_2-CH_2-\underset{\underset{Ar^1}{|}}{N}-Ar^1, \quad (e)$$

-continued $$-CH_2-CH_2-CH_2-\overset{O}{\overset{\|}{C}}-\underset{\underset{Ar^1}{|}}{N}-Ar^1, \quad (f)$$

$$-CH_2-CH_2-CH_2-\underset{\underset{Ar^1}{|}}{N}-\overset{O}{\overset{\|}{C}}-Ar^1 \text{ or} \quad (g)$$

$$-CH_2-CH_2-O-\underset{\underset{Ar^1}{|}}{N}=C-Ar^1, \quad (h)$$

$Ar^1$ is phenyl optionally substituted with halo or $C_{1-4}$alkyloxy;

$Ar^2$ is phenyl optionally substituted with halo or $C_{1-4}$alkyloxy, or pyridinyl;

$R^1$ is $C_{1-4}$alkyl, aminocarbonyl br $(C_{1-4}$alkyl)aminocarbonyl;

Ar is a radical of formula (i) a benzene ring substituted with $R^2$, $R^3$, $R^4$;

(j) a benzene ring substituted with $R^5$, $R^6$;

(k) a benzene ring substituted with $R^7$, $R^8$, $R^9$;

(l) a pyridine ring substituted with $R^{10}$, $R^{11}$, $R^{12}$, $R^{13}$ or (m) a pyridine ring substituted with $R^{14}$, $R^{14}$, $R^{15}$;

$R^2$ and $R^3$ each independently are halo or $C_{1-4}$alkyl;

$R^4$ is hydrogen, halo, nitro, amino, mono- or di($C_{1-4}$alkyl)amino, $C_{1-4}$alkylcarbonylamino, aminocarbonylamino, $C_{1-4}$alkyl, $C_{1-4}$alkyloxy, $C_{1-4}$alkyloxycarbonyl, $C_{1-4}$alkylcarbonyl, aminocarbonyl, mono- or di($C_{1-4}$alkyl)aminocarbonyl, cyano or aminomethyl;

$R^5$ is $C_{1-4}$alkylcarbonyl;

$R^6$ is hydrogen, amino, mono- or di($C_{1-4}$alkyl)amino, $C_{1-4}$alkylcarbonylamino, aminocarbonylamino, aminocarbonyl or cyano;

$R^7$ is $C_{1-4}$alkyl;

$R^8$ is halo or $C_{1-4}$alkylcarbonyl;

$R^9$ is hydrogen or $C_{1-4}$alkyl;

$R^{10}$ is halo or $C_{1-4}$alkyl;

$R^{11}$ is hydrogen, hydroxy or $C_{1-4}$alkyl;

$R^{12}$ is halo or $C_{1-4}$alkyl;

$R^{13}$ is hydrogen or $R^{12}$ and $R^{13}$ taken together may also form a $C_{3-5}$alkanediyl radical;

each $R^{14}$ is $C_{1-4}$alkyl; and $R^{15}$ is $C_{1-4}$alkyl or amino.

In the foregoing definitions the term halo is generic to fluoro, chloro, bromo and iodo; the term $C_{1-4}$alkyl defines straight and branched chain saturated hydrocarbon radicals having from 1 to 4 carbon atoms, such as, for example, methyl, ethyl, propyl, 1-methylethyl, butyl, 1,1-dimethylethyl and the like; the term $C_{3-5}$alkanediyl defines straight and branched chain saturated bivalent hydrocarbon radicals having from 3 to 5 carbon atoms, such as, for example, 1,3-propanediyl, 1,4-butanediyl and 1,5-pentanediyl.

The compounds of formula (I) wherein $R^{11}$ is hydroxy may also exist in the tautomeric oxo-form. Said form, although not explicitly indicated hereinabove, is intended to be included within the scope of the invention.

The compounds of this invention have at least one asymmetric carbon atom in their structure, namely the piperazine carbon atom bearing the $R^1$-radical which may be present in a R- or a S-configuration. Consequently, the compounds of formula (I) may be present in two different enantiomeric forms, which may be separated from each other, for example, by converting the mixture of enantiomers into the acid addition salt form thereof with an optically active acid, separating the diastereomeric salts, e.g., by selective crystallization, and liberating the pure enantiomers by treatment with alkali.

When L has one or more additional chiral centers, each of these chiral centers may be present in the R- or S-configuration and the compounds of formula (I) may have different diastereochemical forms, which may be separated from each other by physical separation methods such as, selective crystallization and chromatographic techniques, e.g. counter current distribution, column-chromatography and the like techniques.

Pure stereochemically isomeric forms may also be derived from the corresponding pure stereochemically isomeric forms of the appropriate starting materials, provided that the reaction occurs stereospecifically. Stereochemically isomeric forms of the compounds of formula (I) are naturally intended to be embraced within the scope of the invention.

The compounds of formula (I) can be used as such or in a pharmaceutically acceptable acid addition salt form, the latter being conveniently obtained by treating the base form with an appropriate acid. Appropriate acids comprise, for example, inorganic acids such as hydrohalic acids, e.g. hydrochloric or hydrobromic acid; sulfuric acid, nitric acid; phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The term acid addition salt form as used hereinabove also comprises the solvates which the compounds of formula (I) and their acid addition salts are able to form. Examples of such solvates are e.g. the hydrates, alcoholates and the like.

Particular compounds for use in the present invention are those compounds wherein $Ar^1$ is phenyl optionally substituted with fluoro or methoxy; and/or $Ar^2$ is phenyl optionally substituted with fluoro or methoxy, or 3-pyridinyl; and/or $R^1$ is methyl, aminocarbonyl or methylaminocarbonyl; and/or Ar is a radical of formula (i), (j), (l) or (m).

More particular compounds are those particular compounds wherein $Ar^1$ is phenyl, 4-fluorophenyl or 4-methoxyphenyl; and/or $Ar^2$ is phenyl, 4-fluorophenyl, 4-methoxyphenyl or 3-pyridinyl; and/or Ar is a radical of formula (i) or (j).

Particularly preferred compounds are those more particular compounds wherein L is 5,5-bis(4-fluorophenyl)pentyl, 5,5-bis(4-fluorophenyl)-4-pentenyl, 5-(4-fluorophenyl)-5-(3-pyridinyl)-4-pentenyl, 4-[N-(4-fluorophenyl)-N-(3-pyridinylcarbonyl)amino]butyl, N,N-bis(4-fluorophenyl) butanamide, 2-[[[bis(4-fluorophenyl)methylen]amino]oxy] ethyl or 3-[(4-fluorophenyl)(3-pyridinyl)methoxy]propyl; and/or $R^1$ is 2-methyl, 3-methyl, 2-aminocarbonyl , 3-aminocarbonyl or 3-methylaminocarbonyl; and/or $R^2$ and $R^3$ are both chloro or methyl; and/or $R^4$ is hydrogen, chloro, nitro, amino, dimethylamino, ethylcarbonylamino, aminocarbonylamino, methoxy, ethoxycarbonyl, acetyl, aminocarbonyl, dimethylaminocarbonyl, cyano or aminomethyl; or $R^5$ is acetyl; and/or $R^6$ is amino, dimethylamino, ethylcarbonylamino, aminocarbonylamino, aminocarbonyl or cyano.

Of particular interest are those enantiomeric forms of the compounds of the above defined groups, which selectively bind and block the nucleoside transport protein of cell membranes.

The most interesting compounds within the present invention are (1)-(−)-2-(aminocarbonyl)-N-(4-amino-2,6-dichlorophenyl)-4-[5,5-bis(4-fluorophenyl)pentyl]-1-piperazineacetamide (I-b), the pharmaceutically acceptable acid addition salt forms thereof and the hydrated forms thereof, in particular the mono- and the hemihydrate thereof. Said most interesting compounds are novel and possess a unique combination of pharmacological selectivity and advantageous characteristics, which is not shared with the previously known N-aryl piperazinealkanamide compounds. Besides being potent, selective nucleoside transport inhibitors, they do not have $Ca^{2+}$-antagonistic properties. Their acute and chronic toxicity is very low. Furthermore, said compounds do not bind to any large extent to plasma proteins and consequently their bioavailability is excellent. Greatly simplifying and broadening their application in therapy, is the fact that they are easily resorbed and thus can be administered orally. In conjunction with the above properties, this convenient route of administering said compounds, renders them particularly suitable for prolonged use, e.g. as prophylactics in high risk patients or in maintenance therapy as set forth hereinafter. A further advantage of using enantiomerically pure compounds resides in the fact that the amount of drug to be administered may be lowered because the undesired inactive enantiomorph is not any longer present. This approach is particularly advantageous as it reduces the likelihood of overdosing and its potentially undesired side-effects such as cardiodepression at said overdoses.

Further most interesting compounds within the present invention are the compounds of formula (I-c), as depicted herebelow, wherein the configuration at the carbon atom bearing the radical $R^1$ is the same as in the abovementioned compound (I-b). The compounds of formula (I-c) are deemed novel too.

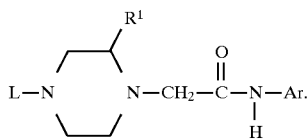

(I-c)

The compounds of formula (I), the stereochemically isomeric forms and the pharmaceutically acceptable acid addition salts thereof, wherein L, R¹ and Ar are as defined hereinabove, and wherein
1) L is a radical of formula (h), or
2) Ar is a radical of formula (m) wherein $R^{15}$ is amino, said compounds being represented by formula (I-a) and said radicals L and Ar being represented respectively by $L^a$ and $Ar^a$

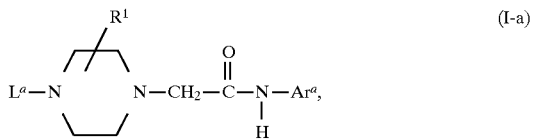

(I-a)

are also novel.

Interesting novel compounds are 3-(aminocarbonyl)-4-[5,5-bis(4-fluorophenyl)pentyl]-N-(6-amino-2,4-dimethyl-3-pyridinyl)-1-piperazineacetamide hemihydrate and 2-(aminocarbonyl)-4-[2-[[[bis(4-fluorophenyl)methylene]amino]oxy]ethyl]-N-(2,6-dichlorophenyl)-1-piperazineacetamide.

A number of compounds of formula (I) as well as their syntheses and their pharmacological properties, are known from U.S. Pat. No. 4,766,125 and EP-A-0,285,219. The novel enantiomerically pure compounds of formula (I) can conveniently be prepared from enantiomerically pure piperazines of formula

(II)

wherein R¹ is as defined under formula (I), and wherein one or two piperazine nitrogen atoms may optionally be protected with a selectively removable group such as, for example, a 1-aryl alkyl group, e.g., phenylmethyl, 1-phenylethyl and the like, an (aryl or $C_{1-4}$alkyl) oxycarbonyl group, e.g. phenoxycarbonyl, methoxycarbonyl, ethoxycarbonyl, tert.butyloxycarbonyl and the like protecting groups. Said protective groups can be removed following art-known procedures, such as hydrogenolysis and hydrolysis.

Said preparation generally involves the consecutive N-alkylation or reductive N-alkylation of each piperazine nitrogen atom with the appropriate L-moiety or N-arylalkanamide moiety following art-known procedures. Typically said preparation proceeds as follows:

(a) in unprotected piperazine derivatives, the most reactive, least sterically hindered nitrogen at the 4-position is N-alkylated first and then the remaining free nitrogen atom at the original 1-position of the starting piperazine is reacted;

(b) in monoprotected piperazine derivatives, the free nitrogen atom is N-alkylated, the protective group is removed and the now unprotected nitrogen atom is reacted; or (c) in bis-protected piperazine derivatives, both protective groups are removed and one proceeds as under (a), or one group is selectively removed, whereupon one proceeds as in (b).

For example, the novel compound (1)-(−)-2-(aminocarbonyl)-N-(4-amino-2,6-dichlorophenyl)-4-[5,5-bis(4-fluorophenyl)pentyl]-1-piperazineacetamide of formula

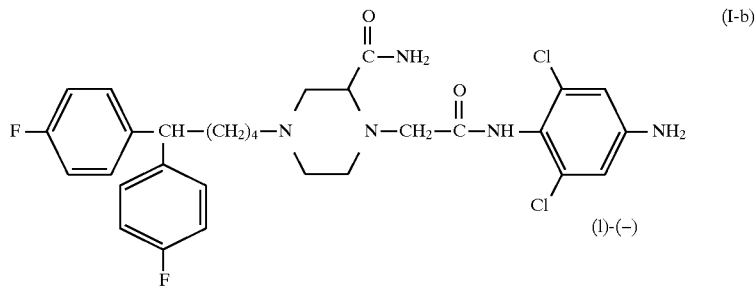

(I-b)

can conveniently be prepared starting from (−)-(S,S)-$N^1,N^2$-bis(1-phenylethyl)-1,2-ethanediamine (II).

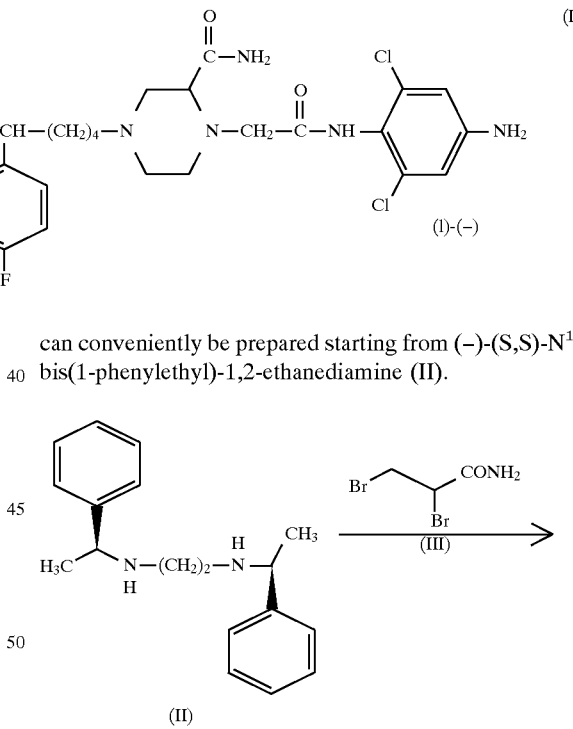

(II)

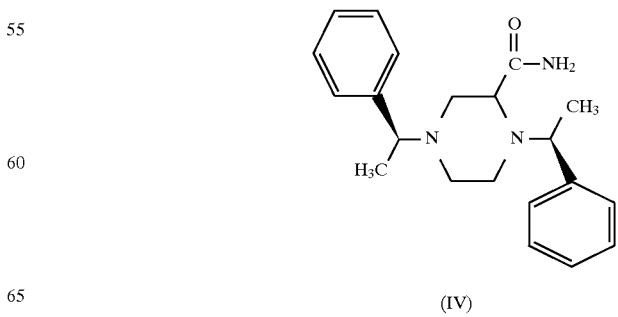

(IV)

The intermediate (II) is cyclized to a piperazine derivative by double N-alkylation with 2,3-dibromopropanamide (III) in a reaction-inert solvent in the presence of a base. Appropriate solvents are aromatic hydrocarbons, e.g. benzene, methylbenzene and the like, halogenated hydrocarbons e.g. tetrachloromethane, chlorobenzene and the like. Suitable bases are alkali and earth alkaline metal carbonates such as, for example, sodium and potassium carbonate. Said cyclization is preferably carried out at the reflux temperature of the reaction mixture.

The intermediate of formula (IV) is converted into the piperazine (+)-(V) by hydrogenolysis under a hydrogen atmosphere in an alkanol such as, for example, methanol, ethanol and the like, and in the presence of a hydrogenation catalyst such as palladium-on-charcoal, platinum-on-charcoal and the like.

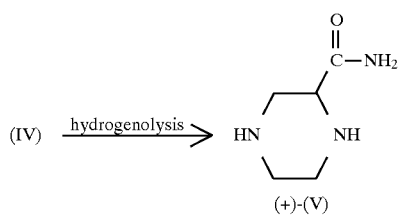

Next the intermediate (+)-(V) is reductively N-alkylated by reaction with 5,5-bis(4-fluorophenyl)pentaldehyde (VI) under a hydrogen atmosphere in an alkanol such as, for example, methanol, ethanol and the like, in the presence of a hydrogenation catalyst such as, for example, palladium-on-charcoal, platinum-on-charcoal and the like. In order to prevent the further reaction of the reaction product it is advantageous to add a catalyst poison such as thiophene to the reaction mixture. In order to enhance the rate of the reaction, the reaction mixture is heated slightly, in particular to about 40° C. to 60° C.

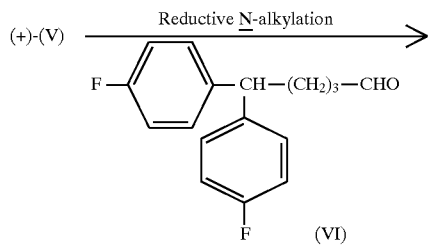

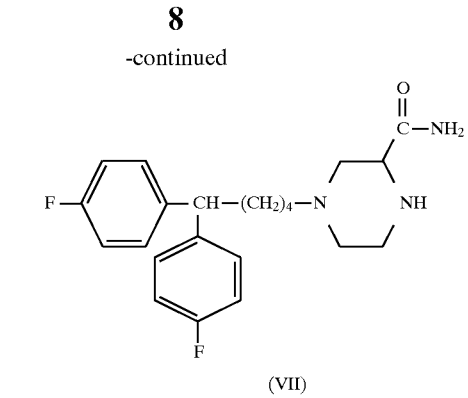

Alternatively, intermediate (VII) can be prepared by N-alkylating intermediate (+)-(V) with a 5,5-bis(4-fluorophenyl)pentane-1-halide or sulfonate of formula

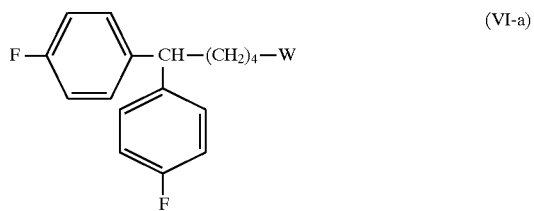

wherein W is halo, e.g. chloro or bromo, or sulfonyloxy, e.g. methanesulfonyloxy, 4-methylbenzenesulfonyloxy and the like. Said alkylation can conveniently be conducted in a reaction-inert solvent such as, for example, an alkanol, e.g. methanol, butanol, cyclohexanol and the like, a dipolar aprotic solvent, e.g. N,N-dimethylformamide, dimethylsulfoxide and the like, in the presence of a base, e.g. an alkali or earth alkaline metal hydroxide, carbonate, e.g. sodium or potassium hydroxide or carbonate.

The thus obtained intermediate (VII) is N-alkylated with a reagent of formula (VIII) wherein W represents a reactive leaving group such as chloro, bromo and the like, in a reaction-inert solvent in the presence of a base.

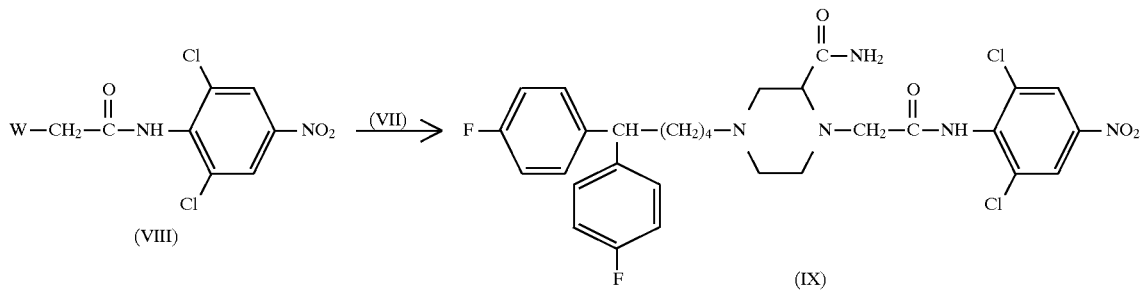

Said N-alkylation reaction can conveniently be conducted by stirring and heating the reactants, in particular by heating at about 70° C. to 100° C. Suitable solvents are, for example, alkanols, e.g., methanol, ethanol, butanol and the like, dipolar aprotic solvents, e.g. N,N-dimethylformamide, dimethyl sulfoxide and the like, or mixtures of said solvents. Appropriate bases are alkali and earth alkaline metal hydroxides, carbonates, hydrogen carbonates and the like, and organic amines, such as, for example, N,N-diethylethanamide, pyridine, morpholine and the like bases. An alkali metal iodide, e.g. potassium iodide may be added in order to enhance the reaction rate.

The intermediate of formula (IX) is finally converted to the novel compound (l)-(−)-(I-b) by a nitro-to-amino reduction step.

oxo-group, following the reaction procedures described in detail hereinabove. The thus obtained intermediate

(VII-a)

is then N-alkylated with an appropriate N-aryl alkanamide of formula

(VIII-a)

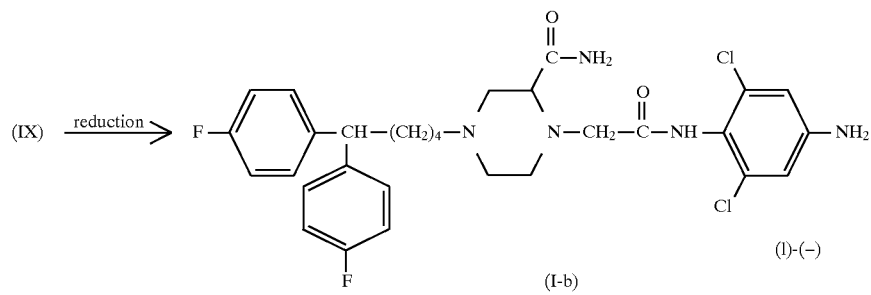

Said reduction can conveniently be conducted in a reaction-inert solvent following art-known reduction procedures. For example, intermediate (IX) may be stirred under a hydrogen atmosphere in an alkanol such as, methanol, ethanol and the like, in the presence of a hydrogenation catalyst such as palladium-on-charcoal, platinum-on-charcoal, Raney nickel and the like. Alternatively said reduction may also be accomplished by treatment of the intermediate (IX) within a reagent such as, for example, sodium sulfite, sodium sulfide, sodium hydrogen sulfide, titanium (III) chloride and the like.

The other novel compounds of formulae (I-a) and (I-c) as defined hereinabove are prepared following the procedure described hereinbefore. Thus, a piperazine of formula (V-a).

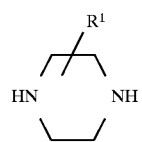

is N-alkylated with an appropriate alkylating reagent L-W (VI-b) or is reductively N-alkylated with a reagent $L^1$=O (VI-c), said $L^1$=O representing a reagent of formula L-H wherein two geminal hydrogen atoms are replaced by an following the N-alkylation procedure described hereinabove.

In all of the preceding reaction steps, the intermediates and final compounds may be isolated and purified following art-known procedures, in particular by liquid chromatography and crystallization.

As previously mentioned the compounds of formula (I) are known to protect the heart from myocardial injury and to improve sleep and counteract sleep disorders. A number of said compounds, more particularly 3-(aminocarbonyl)-4-[4,4-bis(4-fluorophenyl)butyl]-N-(2,6-dichlorophenyl)-1-piperazineacetamide dihydrochloride, monohydrate, generically known as mioflazine, is described as an inhibitor of nucleoside transport through membranes [Molecular Physiology, 8, 615–630 (1985)]. An important, common advantage of the present compounds of formula (I) for use in the methods described hereinbelow is the fact that they are orally active and, contrary to mioflazine, have an excellent bioavailability because they do not generally bind to plasma proteins.

The organ or muscular tissue as mentioned hereinabove in particular is the heart or heart tissue. Typical situations wherein blood reperfusion in said organ or muscular tissue is diminished or absent, comprise, for example, thrombosis and cardioplegia, i.e. arresting a heart before open heart surgery or before transplantation. Reperfusion damage generally occurs whenever blood perfusion is restored to normal after the occurence of any of the above mentioned situations, e.g. upon natural or stimulated thrombolysis or upon reperfusion of the heart after cardioplegia. The term reperfusion damage, also designated reperfusion injury, as used in the instant application defines the damage to tissues and organs which have been previously deprived of blood supply upon reperfusion, i.e. the restoration of blood flow through said tissues and organs. Reperfusion damage is an acute phenomenon which arises immediately upon reperfusion and therefore must be attended to timely.

The amount of active ingredient of formula (I) in the present method is such that effective prevention or limitation of reperfusion damage is obtained upon administration to said organ or muscular tissue.

In a further aspect of the present invention there is a provided method of treating a patient undergoing natural thrombolysis, stimulated thrombolysis (thrombolytic therapy) or reperfusion of the heart after open heart surgery or after receiving a donor heart with an amount, effective in preventing and/or limiting reperfusion damage, of a compound of formula (I) as defined hereinabove.

Thrombolysis as used hereinabove defines the lysis of thrombi, in particular lysis effected by the local action the proteolytic enzyme plasmin within the substance of the thrombi. The term thrombolytic therapy as used herein defines the administration to a patient suffering from a thrombus or thrombi, an effective thrombolytic amount of a thrombolytic agent, optionally followed by a maintenance therapy with an anticoagulant, such as, for example, heparin, ethyl biscoumacetate, ticlopidin and the like. Commonly used thrombolytic agents in said therapy comprise for example, urokinase, streptokinase, tissue plasminogen activator (t-PA), fibrinolysin and the like agents. The present method thus provides a method of preventing or limiting reperfusion damage upon reperfusion following stimulated thrombolysis, said method comprising administering to the patient undergoing thrombolytic therapy an amount of a compound having the formula (I), effective in preventing or limiting reperfusion damage.

More in particular, said method comprises administering to the patient simultaneously, separately or sequentially an effective thrombolytic amount of a thrombolytic agent, particularly a thrombolytic agent specifically mentioned hereinabove, and an effective reperfusion damage preventing and/or limiting amount of a compound having the formula (I). Said method also comprises administering to the patient prophylactically or during maintenance therapy simultaneously, separately or sequentially an effective anticoagulant amount of an anticoagulant agent, particularly an anticoagulant agent specifically mentioned hereinabove, and an effective amount of a compound of formula (I).

The amount of each of the active ingredients, the thrombolytic agent and the compound of formula (I) in the method according to the present invention is such that effective thrombolysis is obtained, concomitant with effective prevention or limitation of reperfusion damage, upon administration to said patients. When maintenance therapy is envisaged, the amount of each of the active ingredients, the anticoagulant agent and the compound of formula (I) in the method according to the present invention is such that effective prevention of formation of thrombi is obtained, concomitant with effective prevention or limitation of reperfusion damage, upon administration of each active ingredient to said patients. The amount of the thrombolytic agent for use in the present method may satisfactorily be equal to the amount of thrombolytic agent commonly used in art-known thrombolytic therapy. For example, streptokinase may be administered in a loading dose of 250,000 to 600,000 units over 30 to 60 minutes, followed by a maintenance dose of about 100,000 units per hour for up to 72 hours, sometimes up to 144 hours; urokinase may be administered by intravenous infusion starting with an initial dose of about 4400 units per kg bodyweight over 10 minutes followed by a maintenance dose of about 4400 units per kg bodyweight each hour for up to 12 hours; tissue plasminogen activator may be administered by intravenous infusion of about 100 mg over 3 hours. The amount of the compound of formula (I) for use in the present method may typically range from about 0.01 to about 100 mg/kg bodyweight, particularly from about 0.1 to about 10 mg/kg bodyweight and more particularly from about 0.2 to about 5 mg/kg bodyweight.

The compounds of formula (I) or the pharmaceutically acceptable acid addition salts thereof may be administered before, during or shortly after the administration of the thrombolytic agent, provided that the time between the administration of the thrombolytic agent and the administration of the compound of formula (I) is such that reperfusion damage is effectively prevented or limited. When simultaneous administration of the thrombolytic agent and a compound of formula (I) is envisaged, a composition containing both a thrombolytic agent and a compound of formula (I) may be particularly convenient. Or, the thrombolytic agent and the compound of formula (I) may be administered separately in the form of suitable compositions. Similarly, when maintenance therapy or prophylaxis with an anticoagulant is envisaged, the compounds of formula (I) may be administered before, during or after the administration of the anticoagulant agent.

The present invention further comprises compositions for preventing or limiting reperfusion damage upon reperfusion following natural or stimulated thrombolysis, or after cardioplegia, said compositions comprising a pharmaceutically acceptable carrier and as active ingredient an effective reperfusion damage preventing or limiting amount of a compound of formula (I).

Compositions for preventing or limiting reperfusion damage upon reperfusion following stimulated thrombolysis may further comprise an effective thrombolytic amount of a thrombolytic agent, in particular a thrombolytic agent specifically mentioned hereinabove.

Compositions for prophylactic use or for maintenance therapy may further comprise an effective anticoagulant amount of an anticoagulant, in particular an anticoagulant specifically mentioned hereinabove.

The amount of each of the active ingredients, the compound of formula (I) and optionally the thrombolytic agent or the anticoagulant, in the foregoing compositions is such that effective prevention or limitation of perfusion damage upon administration is obtained, where applicable concomitant with effective thrombolysis or with effective prevention of coagulation.

Interesting compositions among the groups of compositions described hereinbefore and -after, are those comprising a cyclodextrin (CD) or an ether derivative thereof, as a complexant and/or solubilizer. As examples of such cyclodextrins there may be mentioned $\alpha$-CD, $\beta$-CD, $\gamma$-CD, and ether or mixed ether derivatives thereof. Particular such cyclodextrin derivatives are described in U.S. Pat. No. 3,459,731, EP-A-0,149,197 and EP-A-0,197,571.

Typically such ether or mixed ether derivatives comprise $\alpha$-, $\beta$- or $\gamma$-CD wherein one or more hydroxylgroups are substituted with $C_{1-6}$alkyl, particularly methyl, ethyl or isopropyl; hydroxy$C_{1-6}$alkyl, particularly hydroxyethyl, hydroxypropyl or hydroxybutyl; carboxy$C_{1-6}$alkyl, particularly carboxymethyl or carboxyethyl; or $C_{1-6}$alkyloxycarbonyl$C_{1-6}$alkyl. Especially noteworthy as complexants and/or solubilizers are β-CD, 2,6-dimethyl-β-CD and in particular 2-hydroxypropyl-β-CD, 2-hydroxyethyl-β-CD, 2-hydroxyethyl-γ-CD and 2-hydroxypropyl-γ-CD. In the aforementioned cyclodextrin derivatives, the DS (degree of substitution, i.e. the average number of substituted hydroxy functions per glucose unit) preferably is in the range of 0.125 to 3, in particular 0.3 to 2, more in particular 0.3 to 1. The MS (molar degree of substitution, i.e. the average number of moles of the substituting agent per glucose unit) is in the range of 0.125 to 10, in particular 0.3 to 3 and more in particular 0.3 to 1.5, preferably 0.35 to 0.50. Said compositions may conveniently be prepared by dissolving the cyclodextrin or ether derivative thereof in water and adding thereto a compound of formula (I) as well as other adjuvants and components such as, for example, sodium chloride, potassium nitrate, glucose, mannitol, sorbitol, xylitol and buffers such as, for example, phosphate, acetate or citrate buffers; and optionally concentrating or drying the solution by evaporation under reduced pressure or by lyophilization. The amount of the cyclodextrin or ether derivative thereof in the final composition generally ranges from about 1% to about 40% by weight, particularly from 2.5% to 25% and more particularly from 5% to 20%. The amount of the active ingredient of formula (I) in said final compositions generally ranges from about 0.01% to about 1.0% by weight, particularly from 0.025% to 0.5% and more particularly from 0.05% to 0.2%. Particularly interesting compositions are those comprising (l)-(−)2-(aminocarbonyl)-N-(4-amino-2,6-dichlorophenyl)-4-[5,5-bis(4-fluorophenyl)pentyl]-1-piperazineacetamide as active ingredient and 2-hydroxypropyl-β-cyclodextrin as complexant and/or solubilizer.

To prepare the pharmaceutical compositions of this invention, an effective amount of the active ingredients, in acid or base addition salt form or base form, is combined in intimate admixture with a pharmaceutically acceptable carrier, which can take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid addition salts of (I) due to their increased water solubility over the corresponding base form, are obviously more suitable in the preparation of aqueous compositions.

An especially interesting feature of the compounds of formula (I) for use in the present method is the fact that said compounds can be administered orally thus substantially simplifying the administration of said compounds to high risk patients, more in particular to patients receiving maintenance therapy or anticoagulants.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention further also comprises products containing a compound of formula (I) and a thrombolytic agent as a combined preparation for simultaneous, separate or sequential use in thrombolytic therapy with concomitant prevention or limitation of reperfusion damage. Such products may comprise, for example, a kit comprising a container with a suitable composition containing a compound of formula (I) or a pharmaceutically acceptable acid addition salt thereof and another container containing a composition with a thrombolytic agent. Such a product may have the advantage that a physician wishing to administer thrombolytic therapy with concomitant prevention or limitation of reperfusion damage, can select on the basis of the diagnosis of the patient to be treated, the appropriate amounts of each component and the sequence and timing of the administration thereof.

The term open heart surgery as used herein defines the surgical intervention on a heart temporarily relieved of circulatory function. The method of the present invention particularly provides a method of preventing or limiting reperfusion damage upon reperfusion of the operated heart, said method comprising administering to the patient undergoing open heart surgery an amount of a compound of formula (I) effective in preventing or limiting reperfusion damage. More particularly, said method comprises treating said patient before, during and after surgery with an effective reperfusion damage preventing and/or limiting amount of a compound of formula (I). A particularly advantageous practice consists of arresting the heart whereupon surgery will be performed with a cardioplegic solution comprising an effective reperfusion damage preventing and/or limiting amount of a compound of formula (I).

The term transplantation as used herein defines the transplantation of tissues, in particular of organs and more in particular of hearts from one warm-blooded animal to an identical recipient site within another warm-blooded animal, said warm-blooded animals in particular being humans. The method of the present invention particularly provides a method of preventing or limiting reperfusion damage upon reperfusion of a transplanted heart, said method comprising administering to the patient receiving the donor heart, as well as administering to the heart to be transplanted an effective amount of a compound of formula (I).

More in particular, said method comprises arresting a donor heart for transplantation with a cardioplegic solution, whereby said cardioplegic solution comprises an effective amount of a compound of formula (I), storing said heart in the cold in said cardioplegic solution and transplanting said heart in another subject pre-treated with an effective amount of compound of formula (I) and subsequently reperfusing said heart with oxygenated blood.

The term cardioplegic solution as used herein defined the normal balanced-salt formulations generally used for cardioplegia. Commonly used cardioplegic solutions for arresting a heart comprise for example, hyperkalemic NIH cardioplegic solutions, UW cardioplegic solution, Collins cardioplegic solution M (115 meq $K^+$/L), St. Thomas' Hospital cardioplegic solution, Ringer's injection buffered with tromethamine (3.6%), Plegisol® (Abbott) buffered with sodium hydrogen carbonate injection (8.4%), Modified Krebs high K (34 meq/L) solution and the like cardioplegic solutions. Typical temperatures for storing a heart for transplantation may range from 0° C. to about 10° C., particularly from about 0° C. to about 7° C. and more particularly from about 0° C. to about 4° C.

The amount of each of the active ingredients, the cardioplegic solution and the compound of formula (I), in the method according to the present invention is such that effective cardioplegia is obtained upon administration, concomitant with effective prevention or limitation of reperfusion damage upon reperfusion of the heart whereupon surgery was performed and upon reperfusion of the transplanted heart. For example, the amount of the compound of formula (I) in the cardioplegic solution for use in the present method may typically range from about 0.1 $\mu$M to about 10 $\mu$M, particularly from about 0.5 $\mu$M to about 5 $\mu$M and more particularly from about 0.8 $\mu$M to about 2 $\mu$M.

The amount of the active ingredient, the compound of formula (I), upon administration to the patient receiving a donor heart is such that effective prevention or limitation of reperfusion damage upon reperfusion of the transplanted heart is obtained. For example, the amount of the compound of formula (I) for use in the present method may typically range from about 0.01 to about 100 mg/kg bodyweight, particularly from about 0.1 to about 10 mg/kg bodyweight and more particularly from about 0.2 to about 5 mg/kg bodyweight.

In still a further aspect of the present invention there is provided a method of storing a heart for transplantation in a cardioplegic solution in the cold, which method comprises administering to said cardioplegic solution an amount, effective in prolonging the storage of said heart, of a compound of formula (I) as defined hereinabove.

An especially interesting feature of the present method of storing a heart for transplantation, is the fact that the duration of successfully storing a heart for transplantation in a cardioplegic solution comprising a compound of formula (I) can be prolonged drastically. Whereas a heart for transplantation can be stored successfully for about 4 hours in a usual cardioplegic solution without a compound of formula (I) in the cold, the novel method of storing a heart for transplantation in a cardioplegic solution comprising a compound of formula (I) in the cold allows one to store said heart for at least 24 hours and to transplant said heart subsequently successfully. Thus the present invention further provides a method of storing a heart for transplantation in the cold in a cardioplegic solution, particularly a cardioplegic solution specifically mentioned hereinabove, comprising an effective donor heart protecting amount of a compound of formula (I). The effective donor heart protecting amount of the compound of formula (I) in the cardioplegic solution for use in the present method of storing a heart for transplantation may typically range from about 0.1 $\mu$M to about 10 $\mu$M, particularly from about 0.5 $\mu$M to about 5 $\mu$M and more particularly from about 0.8 $\mu$M to about 2 $\mu$M.

Experimental Part

EXAMPLE 1

Preparation of (−)-2-(aminocarbonyl)-N-(4-amino-2,6-dichlorophenyl)-4-[5,5-bis(4fluorophenyl)-pentyl]-1-piperazineacetamide A mixture of 108.4 parts of (−)-(S,S)-$N^1$,$N^2$-bis(1-phenylethyl)-1,2-ethanediamine, 93.8 parts of 2,3-dibromopropanamide, 334.5 parts of potassium carbonate and 2958 parts of methylbenzene was refluxed for 24 hours using a water separator. The reaction mixture was filtered while hot and the precipitate was partitioned between water and dichloromethane. The organic layer was separated and combined with the filtrate. The whole was dried, filtered and evaporated. The residue was purified by column chromatography (Lichroprep RP18; $H_2O$ (0.5% $CH_3COONH_4$)/$CH_3CN$ 55:45). The eluent of the desired fraction was evaporated, yielding 20.8 parts (15.4%) of [1(S),2(S),4(S)]-1,4-bis(1-phenylethyl)-2-piperazinecarboxamide (interm. 1).

A mixture of 20.8 parts of intermediate (1) and 198 parts of methanol was hydrogenated at normal pressure and room temperature with 2 parts of palladium-on-charcoal catalyst 10%. After the calculated amount of hydrogen was taken up, the catalyst was filtered off and the filtrate was evaporated, yielding 7.8 parts (98.0%) of (+)-2-piperazinecarboxamide (interm. 2).

A mixture of 3.9 parts of intermediate (2), 8.3 parts of 5,5-bis(4-fluorophenyl)pentaldehyde, 2 parts of a solution of thiophene in methanol (4%) and 198 parts of methanol was hydrogenated at normal pressure and 50° C. with 2 parts of palladium-on-charcoal catalyst 10%. After the calculated amount of hydrogen was taken up, the catalyst was filtered off and the filtrate was evaporated. The residue was converted into the ethanedioate salt in ethanol. The salt was recrystallized from a mixture of ethanol and methanol. The product was filtered off and dried, yielding 8.82 parts (61.6%) of (+)-4-[5,5-bis(4-fluorophenyl)pentyl]-2-piperazinecarboxamide ethanedioate (1:1); $[\alpha]_D^{20}$=+10.02° (conc.=0.5% in DMF) (interm. 3).

8.82 Parts of intermediate (3) were taken up in water and converted into the free base with $NH_4OH$. The base was extracted with dichloromethane (3×) and the combined extracts were dried, filtered and evaporated. To the residue there were added 6.5 parts of 1-chloro-N-(2,6-dichloro-4-nitrophenyl)acetamide, 3.75 parts of N,N-diethylethanamine and 113 parts of N,N-dimethylformamide. The whole was stirred over weekend at 70° C. and was then evaporated. The residue was partitioned between $NaHCO_3$ (5% aq.) and dichloromethane. The organic layer was separated, dried, filtered and evaporated. The residue was purified by column chromatography (silica gel; $CH_2Cl_2$/($CH_2Cl_2$+10% $CH_3OH$) 70:30). The eluent of the desired fraction was evaporated and the residue was converted into the hydrochloride salt in 2-propanol. The product was filtered off and dried in vacuo at 50° C., yielding 3.78 parts (30.5%) of (−)-2-(aminocarbonyl)-4-[5,5-bis(4-fluorophenyl)pentyl]-N-(2,6dichloro4-nitrophenyl)-1-piperazineacetamide monohydrochloride; $[\alpha]_D^{20}$=−18.47° (conc.=0.5% in CH$_3$OH) (interm. 4).

A mixture of 3.6 parts intermediate (4), 1 part of a solution of thiophene in methanol (4%) and 119 parts of methanol was hydrogenated at normal pressure and room temperature with 2 parts of palladium-on-charcoal catalyst 10%. After the calculated amount of hydrogen was taken up, the catalyst was filtered off and the filtrate was evaporated. The residue was purified by column chromatography (Lichroprep RP-18; H$_2$O (0.5% CH$_3$COONH$_4$)/CH$_3$OH/CH$_3$CN 40:20:40). The desired fractions were concentrated and the product was allowed to crystallize from the resulting aqueous solution. It was filtered off and dried in vacuo at 60° C., yielding 1.49 parts (43.4%) of (−)-2-(aminocarbonyl)-N-(4-amino-2,6-dichlorophenyl)-4-[5,5-bis(4-fluorophenyl)pentyl]-1-piperazineacetamide hemihydrate; mp. 123.4° C.; $[\alpha]_D^{20}$=−29.63° (conc.=0.5% in CH$_3$OH) (comp. I-b).

EXAMPLE 2

Biological Example

Dog hearts were arrested either with hyperkalemic NIH cardioplegia (group I, n=6) or with the same cardioplegia after addition of 2-(aminocarbonyl)-N-(4-amino-2,6-dichlorophenyl)-4-[5,5-bis(4-fluorophenyl)pentyl]-1-piperazineacetamde (group II, n=6). The hearts were stored cold for 24 hours at 0°–5° C. (ice-water) in the cardioplegic solution and then transplanted orthotopically. To the recipient dogs was administered 0.1 mg/kg bodyweight of 2-(aminocarbonyl)-N-(4-amino-2,6-dichlorophenyl)-4-[5,5-bis(4-fluorophenyl)pentyl]-1-piperazineacetamide before transplantation. Myocardial content of high energy phosphates (HEP) was determined in serial biopsies. In group I ATP was 50% and CrP 18% of control after 24 hours storage. During 60 minutes reperfusion on cardiopulmonary bypass (CPB) HEP content decreased (p<0.05) and all animals developed a "stone heart" after transplantation. After 24 hours storage in group II ATP was 82% and CrP 28% of control (p<0.05 vs. group I). After transplantation HEP content remained stable and all hearts could be weaned from CPB without inotropic support except for isoprenaline. Thus, optimal myocardial preservation was obtained with the combination of cardioplegia and nucleoside transport inhibition.

EXAMPLE 3

Composition Examples

1. Injectable Solution

| active ingredient * | 1 g |
|---|---|
| hydrochloric acid 0.1N | 0.04 l |
| 2-hydroxypropyl-β-cyclodextrin | 50 g |
| sodium chloride | 5.5 g |
| sodium hydroxide 1N | ad pH 3.7–3.9 |
| water | ad 1 l |

* 2-(aminocarbonyl)-N-(4-amino-2,6-dichlorophenyl)-4-[5,5-bis(4-fluorophenyl)-pentyl]-1-piperazineacetamide.

Method of preparation 50 g of HP-β-cyclodextrin are dissolved in 0.5 l of water. There are added successively 0.04 l of hydrochloric acid 0.1N and 1 g of 2-(aminocarbonyl)-N-(4-amino-2,6-dichlorophenyl)-4-[5,5-bis(4-fluorophenyl)pentyl]-1-piperazineacetamide. The whole is stirred until a clear solution is obtained. After diluting with water to 0.9 l, there are dissolved 5.5 parts of sodium chloride with stirring. The acidity is adjusted with sodium hydroxide 1N to pH 3.7–3.9. The solution is diluted with water to 1 l, thus yielding an injectable solution containing 1 mg/ml of active ingredient.

2. Oral Solution

| active ingredient * | 1 g |
|---|---|
| 2-hydroxypropyl-β-cyclodextrin | 50 g |
| hydrochloric acid 0.1N | 0.04 l |
| sorbitol 70% | 0.1 l |
| propyleneglycol | 0.1 l |
| disodium ethylenediaminetetraacetate | 2 g |
| benzoic acid | 3 g |
| mouth wash flavour | 1 g |
| sodium hydroxide 1N | ad pH 4.0 |
| purified water | ad 1 l |

* 2-(ammocarbonyl)-N-(4-amino-2,6-dichlorophenyl)-4-[5,5-bis(4-fluorophenyl)-pentyl]-1-piperazineacetamide.

Method of preparation 50 g of HP-β-cyclodextrin are dissolved in 0.6 l of water. There are added successively 0.04 l of hydrochloric acid 0.1N and 1 g of 2-(aminocarbonyl)-N-(4-amino-2,6-dichlorophenyl)4-[5,5-bis(4-fluorophenyl)pentyl]-1-piperazineacetamide. The whole is stirred until a clear solution is obtained. There are dissolved 2 g of Na$_2$(EDTA) with stirring and then there is added 0.1 l of sorbitol 70%. To the homogeneous solution there are successively added a solution of 3 g of benzoic acid in 0.1 l of propyleneglycol and 1 g of mouth wash flavour. The acidity is adjusted with sodium hydroxide 1N to pH 3.7–3.9. The solution is diluted with water to 1 l, thus yielding an oral solution containing 1 mg/ml of active ingredient.

We claim:

1. A process of preparing the compound (1)-(−)-2-aminocarbonyl)-N-(4-amino-2,6-dichlorophenyl)-4-[5,5-bis(4-fluorophenyl)-pentyl]-1-piperazineacetamide (I-b)

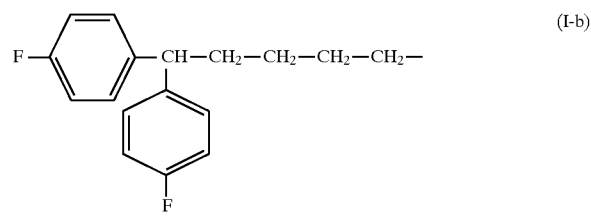

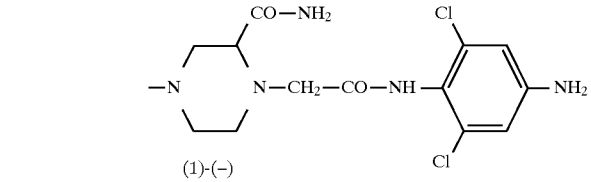

characterized by, a) cyclizing(−)-(S,S)-N$^1$,N$^2$-bis(1-phenylethyl)-1,2-ethanediamine (II) with 2,3-dibromopropanamide (III) in a reaction-inert solvent in the presence of a base, thus yielding an intermediate of the formula:

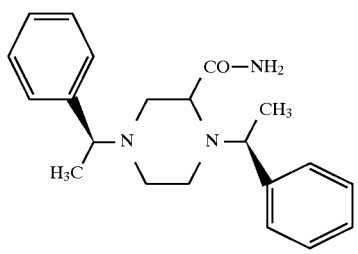

b) separating the intermediate of Formula (IV) into two stereoisomers and recovering thereby [1(S),2(S),4(S)]-1,4-bis(1-phenylethyl)-2-piperazinecarboxamide;

c) hydrogenolyzing said [1(S),2(S),4(S)]-1,4-bis(1-phenylethyl)-2-piperazinecarboxamide under a hydrogen atmosphere in an alkanol in the presence of a hydrogenation catalyst to produce (+)-2-piperazinecarboxamide (V);

d) reductively N-alkylating said (+)2-piperazinecarboxamide (V) with 5,5-bis(4-fluorophenyl)pentaldehyde (VI) under a hydrogen atmosphere in an alkanol in the presence of a hydrogenation catalyst to produce a compound of the formula:

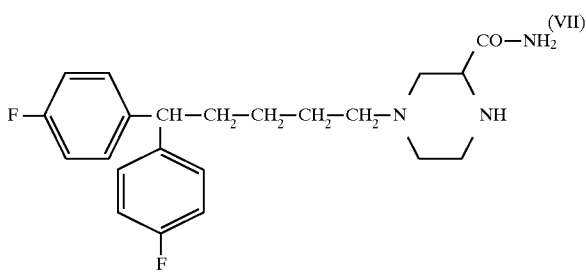

e) N-alkylating the compound of Formula (VII) with an alkylating reagent of the formula:

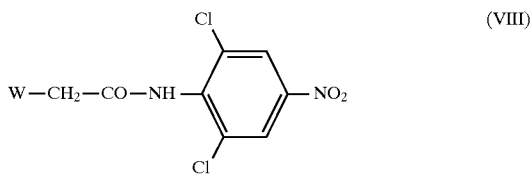

wherein W represents a reactive leaving group, in a reaction-inert solvent in the presence of a base to form a compound of the formula:

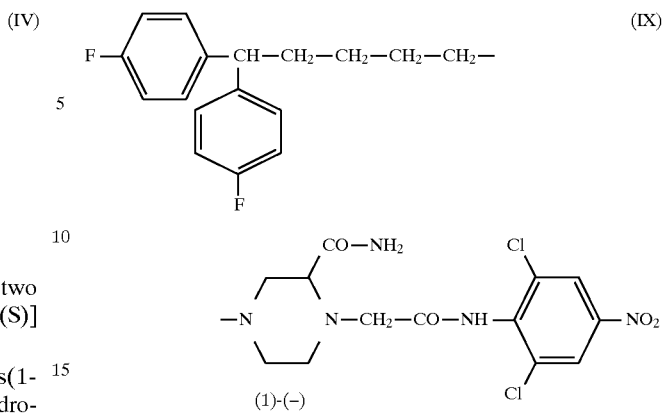

and f) reducing the compound of formula (IX) in the presence of a reducing agent in a reaction-inert solvent.

2. A process according to claim 1, wherein W is chloro or bromo.

3. A process according to claim 1, wherein the reaction inert solvent of step a) is an aromatic hydrocarbon or halogenated hydrocarbon.

4. A process according to claim 3, wherein the reaction inert solvent of step a) is benzene, methylbenzene, tetrachloromethane or chlorobenzene.

5. A process according to claim 1, wherein the base of step a) is an alkali or alkaline earth metal carbonate.

6. A process according to claim 1, wherein the reaction of step a) occurs at reflux temperature of the reaction mixture.

7. A process according to claim 1, wherein the hydrogenation catalyst is palladium-on-charcoal or platinum-on-charcoal.

8. A process according to claim 1, wherein the reaction inert solvent of step e) is an alkanol, dipolar aprotic solvent, or mixture thereof.

9. A process according to claim 8, wherein the reaction inert solvent of step e) is methanol, ethanol, butanol, N,N-dimethylformamide, dimethyl sulfoxide or a mixture thereof.

10. A process according to claim 1, wherein the base of step e) is an alkali or alkaline earth metal hydroxide, carbonate, hydrogen carbonate or organic amine.

11. A process according to claim 10, wherein the base of step e) is N,N-diethylethanamide, pyridine, or morpholine.

* * * * *